United States Patent [19]

Fu

[11] Patent Number: 4,495,093

[45] Date of Patent: Jan. 22, 1985

[54] PROCESS FOR MAKING THIOBISCARBAMATES

[75] Inventor: Wallace Y. Fu, Chapel Hill, N.C.

[73] Assignee: Union Carbide Corporation, Danbury, Conn.

[21] Appl. No.: 368,639

[22] Filed: Apr. 15, 1982

[51] Int. Cl.³ .......................................... C07C 103/12
[52] U.S. Cl. ................................................. 260/453.3
[58] Field of Search ..................................... 260/453.3

[56] References Cited

U.S. PATENT DOCUMENTS 4,323,516  4/1982  Ashworth et al. ............... 260/453.3

OTHER PUBLICATIONS

Conrow & McDonald, Deductive Organic Chemistry, Addison-Wesley Pub. Co., Inc. Reading Mass., 1966, p. 116.

Primary Examiner—Henry R. Jiles
Attorney, Agent, or Firm—Clement J. Vicari

[57] ABSTRACT

An improved method for the preparation of stable, thiobiscarbamates in high yields and high purity is provided which involves the in situ reaction of a carbamate with a sulfur chloride in the presence of a nitrogen-containing heterocyclic base and thereafter quenching and washing the reaction slurry with an alcohol at low temperatures.

19 Claims, No Drawings

PROCESS FOR MAKING THIOBISCARBAMATES

FIELD OF THE INVENTION

This invention relates to an improved process for preparing stable, thiobiscarbamates in high yields. In one aspect, this invention is directed to an improved process for the preparation of thiobiscarbamates which involved the in situ reaction of a carbamate with sulfur dichloride in the presence of a nitrogen-containing heterocyclic base and thereafter quenching and washing the slurry with methanol at low temperatures. In another aspect this invention relates to an improved process for the preparation of bis-[O-(1-methylthioethylimino)-N-methylcarbamic acid]-N,N'-sulfide.

BACKGROUND OF THE INVENTION

Prior to present invention several processes had been disclosed in the literature for the preparation of thiobiscarbamates. For example U.S. Pat. No. 4,004,031 which issued on Jan. 18, 1977 to Jozef Drabek, disclosed the preparation of bis-]O-(1-alkylthioethylimino)-N-methylcarbamic acid]-N,N'-sulfides which were indicated to be useful as insecticides. However, it has been subsequently observed that this method results in relatively low yields of the desired sulfide and high yields of undesired by-products. Moreover, it has also been observed that the product is not sufficiently stable and hence coupled with low yields it is unattractive for large scale production as a commercial pesticide.

In U.S. Pat. No. 4,256,655 which issued on March 17, 1981 to R. W. Ashworth and W. Y. Fu there is also disclosed a method for making thiobiscarbamates which involves the preparation of a nitrogen-containing heterocyclic base with a sulfur chloride and thereafter, in the presence of a solvent reacting this pre-formed adduct with a carbamate. While this method represented a substantial improvement in yield of the desired thiobiscarbamate, over earlier methods, the stability of the product for commercial use was still not reliable.

In applicant's copending application Ser. No. 199,382 filed on Oct. 21, 1980 now U.S. Pat. No. 4,323,516, , a further improvement to the method for making thiobiscarbamates is provided. The method disclosed therein also involves the pre-formation of an adduct of solvent and sulfur chloride and thereafter reacting the adduct with the carbamate and washing the reaction product with water or alcohol.

Prior to the present invention, however, none of these methods gave a product in sufficiently high yield and of acceptable stability to be commercially attractive. Accordingly, one or more of the following objects can be achieved by the practice of this invention. It is an object of this invention to provide an improved process for the preparation of thiobiscarbamates which exhibit excellent stability characteristics. Another object of this invention is to provide an improved process for the preparation of thiobiscarbamates in high yields. A further object of this invention is to provide a process which involves the in situ reaction of a carbamate with sulfur dichloride in the presence of a nitrogen-containing heterocyclic base. A still further object is to provide a process for the preparation of thiobiscarbamates wherein the reaction is quenched with methanol at low temperatures. Another object of this invention is to provide an improved process for the preparation of bis-[O-(1-methylthioethylimino)-N-methylcarbamic acid]-N,N'-sulfide in high yields and which is sufficiently stable for commercial applications. These and other objects will readily become apparent to those skilled in the art in light of the teachings hereinsetforth.

SUMMARY OF THE INVENTION

In general, the invention relates to an improved method for the preparation of a stable thiobiscarbamate of the formula:

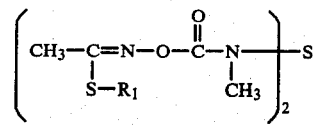

wherein
$R_1$ is alkyl of from 1 to 4 carbon atoms.
The process comprises the steps of:
(1) contacting at a temperature of from about 0° C. to about 35° C.
  (a) a mixture of:
    (i) a nitrogen-containing heterocyclic base, and
    (ii) a carbamate of the formula:

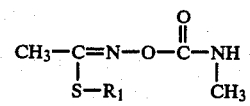

wherein $R_1$ is a previously defined, with
  (b) a sulfur chloride of the group of $SCl_2$ and $S_2Cl_2$, to form a reaction slurry
(2) cooling the slurry to a temperature of no greater than about 20° C.,
(3) quenching the slurry by the addition thereto of a $C_1$–$C_3$ alcohol,
(4) separating the thiobiscarbamate from the slurry and purifying it by one or more washings with methanol, and
(5) thereafter, recovering the thiobiscarbamate in high yield, and wherein the thiobiscarbamate is thermally stability for prolonged storage.

DETAILED DESCRIPTION OF THE INVENTION

As previously indicated the invention involves the in situ reaction of a carbamate with sulfur chlorides in the presence of a nitrogen-containing heterocyclic-base preferably pyridine, and thereafter quenching and washing the reaction slurry with a $C_1$–$C_3$ alcohol at low temperatures. It has been observed, that when the thiobiscarbamates are prepared in accordance with the teachings of this invention, that the desired product is obtained in relatively high yields, has a high degree of purity and, is sufficiently stable for prolonged storage and hence useful as a commercial insecticide.

As illustrative of the process of this invention is the preparation of bis-[O-(1-methylthioethylimino)-N-methylcarbamic acid]-N,N'-sulfide from methyl (methyliminocarbonyloxy)-ethanimidothioate (methomyl) in accordance with the following equation:

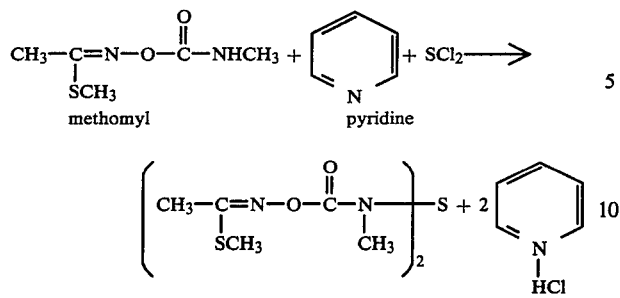

While sulfur dichloride is the preferred sulfur chloride, this compound decomposes slowly according to the equation

Hence commercial $SCl_2$, which currently is believed to contain roughly 70 to 85% $SCl_2$, is a practical and acceptable sulfur chloride. Sulfur monochloride, $S_2Cl_2$, is also acceptable, as are mixtures of $SCl_2$ and $S_2Cl_2$.

The reaction between the carbamate, pyridine and sulfur chloride is preferably carried out for about 0.25 to 4 hours of addition of reactants at temperatures between about $-10°$ and $35°$ C. Additional reaction time is about 20 min to 4 hours.

Prior to the present invention is was not possible to prepare thiobiscarbamate by the known processes with a high degree of confidence that the product would be sufficiently stable for storage, shipment, and use as a commercial product. Thiobiscarbamate prepared by earlier processes occasionally decomposed to gaseous products during or soon after drying at elevated temperatures. Hence a procedure was needed wherein the desired characteristics could be achieved. The present invention provides a novel process whereby the resulting thiobiscarbamate product is obtained in high yields, has a high degree of purity and is sufficiently stable to be attractive for commercial applications.

It has been noted that in products prepared by previous methods that several potential process contaminants reduce the stability of the said thiobiscarbamate. For example, reaction by-products such as pyridine, pyridine hydrochloride, methomyl and methomyl oxime could reduce the product stability.

As in certain of the earlier processes for the preparation of the thiobiscarbamates, pyridine is the preferred reaction media for the process of this invention. However, in the instant process the pyridine participates in the reaction by forming a complex with sulfur dichloride in situ, and that complex reacts with the carbamate. The process provides the thiobiscarbamate in high yields and purity of greater than 95 percent. Moreover, it has been observed that the product is sufficiently stable to be shipped and stored. Thiobiscarbamates produced by the earlier known processes were not characterized by uniform high stability, and hence, were not commercially attractive.

As indicated, the use of pyridine as the reaction medium gave the most satisfactory results. The yields of the observed thiobiscarbamate were consistently above 80 percent based upon the carbamate starting material. Moreover, when methanol is used as the quenching and washing medium, excellent purity and stability are obtained. Additionally, there are other advantages to using pyridine as the reaction medium. The carbamate starting material, particularly methomyl, is quite soluble in pyridine whereas the desired thiobiscarbamate is moderately soluble and crystallizes. Moreover, the reaction in pyridine is much faster than in solvents such as xylene and large crystals can be grown by controlling the reactant feed rate.

The stoichiometric relationship between methomyl and pyridine was studied and it was observed that the weight ratio of methomyl and pyridine should preferably be within the weight ratio of from about 1:2 to about 1:4.

In practice, since the reaction is exothermic, it is preferred to add the sulfur chloride gradually to the mixture of pyridine and carbamate so that overall reaction temperature is no greater than about 35° C.

It was also observed that the alcohol was necessary as the quench liquid and as the solvent for reslurrying the thiobiscarbamate if a product of high stability was desired. The use of a $C_1-C_3$ alcohol instead of water also reduces the drying time of the final product and hence affects the economics of the overall process. Alcohol is also a better solvent for the removal of impurities and pyridine hydrochloride by product.

After the reaction is completed, the reaction slurry is quenched by the addition of the alcohol. Thereafter, the thiobiscarbamate is separated from the slurry by conventional separation techniques, such as filtration, centrifugation or the like. Finally, the reaction product is washed one or more times with the cooled alcohol and dried.

The test employed for the determination of stability is known as the 160° C. Accelerated Stability Test. This test is a modification of the Geigy-Kuhner test and provides a non-subjective quick assessment to stability of the thiobiscarbamate. The test is conducted by measuring and recording the temperature of 2 grams of sample in a test tube and 2 grams of reference material in another test tube, both of which are kept in a constant-temperature heated aluminum block. As the sample decomposes, gas is evolved rapidly and the heat of reaction causes an exotherm in the sample and the gas space above the sample. The stability times for samples prepared by the process of this invention are in the range of 80 to 180 minutes at 160° C.

The following examples illustrate the best mode presently contemplated for the practice of this invention.

EXAMPLE 1

Pyridine (300 g, 3.79 moles) and methomyl (107 g, 0.66 mole) were combined and stirred in a 1-liter resin flask. The endothermic process of dissolving methomyl in pyridine lowered the solution temperature from 20° C. to 12° C. Sulfur dichloride (47.2 g, 0.33 mol, 72% assay) was placed in a glass addition funnel equipped with a teflon needle valve. The pyridine solution was moderately stirred under an inert nitrogen atmosphere at 20°-25° C. while sulfur dichloride was added in 3 hours. The coupling reaction slurry was stirred at 20°-25° C. for an additional 3 hours.

The reaction slurry was quenched with cold methanol and filtered. The filter cake was washed with fresh cold methanol and filtered. The wet cake was transferred into a stirred vessel containing methanol. After 20 minutes of mixing the slurry was filtered again and washed with fresh cold methanol. The wet cake was then vacuum dried to give 99.46 gram (85.0% isolated) of product.

Analysis by HPLC showed 96.07% assay and 1.50% sulfur. An absolute yield of 81.7% (85.0×96.07% assay) was obtained with this batch.

EXAMPLES 2-6

In order to demonstrate the improvements obtained by conducting the process in accordance with the teachings of the instant invention, five other variations of the process were examined: (1) in situ reaction, water quench and water reslurry; (2) in situ reaction, water quency and methanol reslurry; (3) pre-complexation reaction, water quench and methanol reslurry; and (5) pre-complexation reaction, methanol quench and methanol reslurry.

Among the six variations, the in situ, methanol quench and methanol reslurry of this invention provided the best results with simpler operation. Product yield, product stability, crystal size, impurity concentrations were all interrelated to provide the preferred method for preparation of the thiobiscarbamate.

All the experiments were conducted with the same quantities of reactants. For example, the amount of pyridine in the in situ process (150 g, 3.00 units) is the same as in the pre-complexing process (90 g or 1.8 units in the complexation, 60 g or 1.2 units in the coupling). The sulfur dichloride was calculated to be 0.169 mol (75.6% assay) with 0.041 mol (23.6%) of $S_2Cl_2$.

The conditions employed and the results obtained are set forth in Tables I–III below:

TABLE I

| Examples | Variation of Process Conditions | | |
|---|---|---|---|
| | Reaction | Quench | Reslurry |
| 2 | Pre-complexing | Water | Water |
| 3 | Pre-complexing | Water | Methanol |
| 4 | Pre-complexing | Methanol | Methanol |
| 5 | In Situ (no pre-complexing) | Water | Water |
| 6 | In Situ (no pre-complexing) | Water | Methanol |

Reaction Conditions

Pre-complexing The pyridine-sulfur dichloride complex was prepared by adding 0.46 unit of sulfur dichloride (75% assay) at room temperature to 1.80 units of 0° C. pyridine. The exotherm was controlled by a cooling bath at −20° C. and by moderating the $SCl_2$ feed rate. A solution of 1.07 unit of methomyl in 1.20 units or pyridine at 15° C. was then added slowly during 20–30 minutes to the complex which was warmed to 20°–25° C. The reaction temperature was maintained at 20°–25° C. for a period of 4–5 hours and then cooled to 10° C. before quenching.

In situ A solution of methomyl (1.07 unit) and pyridine (3.00 unit) was prepared. The dissolution was endothermic. The solution eventually self-cooled to 12° C. Sulfur dichloride (0.46 unit) at room temperature was added during 10–15 minutes while the reaction temperature was maintained between 20°–25° C. with exthermal cooling (0° C. bath). The reaction temperature of 20°–25° C. was maintained for another 4–5 hours and then cooled to 10° C. before quenching.

Quench Conditions

Water Water (6.00 units) at 5°–10° C. was added to the reaction slurry in 10 minutes. A very mild exotherm of 1° C. was noted during the first 5–10 mL of water addition. The resulting slurry was stirred for 20 minutes at 10° C. and filtered. The filtered cake was washed with 3.00 units of cold water. The filtered wet cake was then reslurried as above.

Methanol Methanol (6.00 units) at −5° C. was added to the reaction slurry in 10 minutes. A very mild exotherm of 1° C. was noted during the first 5–10 mL of methanol addition. The quench slurry was stirred for 20 minutes at −5° C. and filtered. The filtered cake was washed with 3.00 units of −5° C. methanol. The filtered wet cake was then reslurried.

Reslurry Conditions

Water The filtered wet cake was placed in an erlenmeyer flask and reslurried with 3.00 units of 5°–10° C. water for 20 minutes and then filtered using maximum vacuum (simulating centrifuge conditions to reduce volatiles on wet cake). The cake was washed on the filter twice with 3.00 units of 5°–10° C. water each. The wet cake was transferred to a porcelain dish and dried.

Methanol The filtered wet cake was placed in an erlenmeyer flask and reslurried with 3.00 units of −5° C. methanol for 20 minutes and then filtered. The cake was washed on the filter twice with 3.00 units of −5° C., methanol each. The wet cake was transferred to a porcelain dish and dried.

The rest of the process conditions were held constant.

TABLE II

YIELD AND STABILITY OF THIOBISCARBAMATE PRE-COMPLEX PYRIDINE PROCESS

| | % ABS YLD | AST TEST | SULFUR | % PYR HCl | ASSAY | M.P. |
|---|---|---|---|---|---|---|
| Water Quench | 87.8 | <80 | 2.94 | .05 | 96.04 | 166-8 |
| Water Reslurry | 85.8 | <80 | 3.00 | .06 | 96.15 | 168-9 |
| | 87.0 | <80 | 2.25 | .03 | 97.45 | 168-9 |
| | 85.2 | <80 | 2.54 | .02 | 96.92 | 167-8 |
| Average | 86.45 | <80 | 2.68 | .04 | 96.64 | — |
| Water Quench | 83.8 | <80 | 2.76 | .01 | 96.90 | 168-9 |
| MeOH Reslurry | 86.9 | <80 | 2.74 | .01 | 96.94 | 168-9 |
| | 83.9 | <80 | 3.14 | .01 | 96.20 | 167-8 |
| Average | 84.87 | <80 | 2.88 | .01 | 96.68 | — |
| MeOH Quench | 82.9 | >100 | 1.32 | .01 | 98.38 | 169-170 |
| MeOH Reslurry | 84.2 | >100 | 1.30 | .01 | 98.43 | 169-170 |
| | 82.5 | >100 | 1.84 | .01 | 97.83 | 170-1 |
| | 83.9 | >100 | 1.93 | .01 | 97.71 | 169-170 |
| | 79.7 | >100 | 1.16 | .01 | 98.31 | 169-170 |
| Average | 82.64 | >100 | 1.51 | .01 | 98.13 | — |

AST = 160° C. Accelerated Stability Test.

TABLE III

YIELD AND STABILITY OF THIOBISCARBAMATE IN SITU PYRIDINE PROCESS

| | % ABS YLD | AST TEST | SULFUR | ASSAY | M.P. | % PYR HCl |
|---|---|---|---|---|---|---|
| Water Quench | 81.3 | <80 | 2.29 | 95.90 | 166–8 | .10 |
| Water Reslurry | 79.3 | <80 | 2.02 | 96.79 | 169–170 | .02 |
| | 80.2 | <80 | 2.66 | 97.95 | 167–8 | .53 |
| | 84.4 | <80 | 2.62 | 96.67 | 166–7 | .04 |
| | 86.6 | <80 | 2.98 | 96.33 | 165–6 | .03 |
| Average | 82.4 | <80 | 2.51 | 96.73 | — | .15 |
| Water Quench | 83.1 | <80 | 2.86 | 96.10 | 165–6 | .04 |
| MeOH Reslurry | 82.8 | <80 | 2.43 | 96.82 | 166–7 | .03 |
| | 80.3 | <80 | 2.43 | 96.70 | 167–8 | .02 |
| Average | 82.1 | <80 | 2.57 | 96.54 | — | .03 |
| MeOH Quench | 82.4 | >100 | 2.76 | 96.86 | 169–170 | .02 |
| MeOH Reslurry | 83.6 | >100 | 2.48 | 97.01 | 168–9 | .03 |
| | 82.2 | >100 | 2.78 | 96.71 | 169–170 | .02 |
| Average | 82.73 | >100 | 2.67 | 96.86 | — | .02 |

AST = 160° C. Accelerated Stability Test.

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. An improved method for the preparation of a stable thiobiscarbamate compound of the formula:

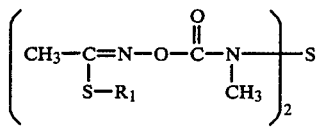

Formula I wherein $R_1$ is alkyl of from 1 to 4 carbon atoms, which method comprises the steps of:

(1) contacting at a temperature of from about 0° C. to about 35° C.
    (a) a mixture of:
        (i) a nitrogen-containing heterocyclic base, and
        (ii) a carbamate of the formula:

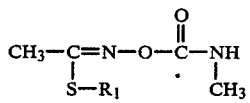

Formula II wherein $R_1$ is as previously defined, with
    (b) a sulfur chloride of the group of $SCl_2$ and $S_2Cl_2$, to form a reaction slurry.

(2) cooling said slurry to a temperature of no greater than about 20° C., (3) quenching said slurry by the addition thereto of a $C_1$–$C_3$ alcohol at a temperature of no greater than 35° C., (4) separating said thiobiscarbamate from said slurry and purifying by one or more washings with methanol, and (5) thereafter, recovering said thiobiscarbamate in high yield, and having a good thermal stability.

2. The methanol of claim 1 wherein said alcohol is methanol.

3. The method of claim 1 wherein $R_1$ is methyl.

4. The method of claim 1 wherein $R_1$ is ethyl.

5. The method of claim 1 wherein $R_1$ is n-propyl.

6. The method of claim 1 wherein $R_1$ is iso-propyl.

7. The method of claim 1 wherein $R_1$ is n-butyl.

8. The method of claim 1 wherein $R_1$ is secondary-butyl.

9. The method of claim 1 wherein $R_1$ is tertiary-butyl.

10. The method of claim 1 wherein said nitrogen-containing heterocyclic base is pyridine.

11. The method of claim 1 wherein said chloride is sulfur monochloride.

12. The method of claim 1 wherein said chloride is sulfur dichloride.

13. The method of claim 1 wherein said carbamate is methyl (methyliminocarbonyloxy)-ethanimidothioate.

14. The method of claim 1 wherein the temperature in step 1 is from about 20° C. to about 25° C.

15. The method of claim 1 wherein said sulfur chloride is gradually added to said mixture of said nitrogen-containing heterocyclic base and said carbamate.

16. An improved method for the preparation of bis-[O-(1-methylthioethylimino)-N-methylcarbamic acid]-N,N'-sulfide which method comprises the steps of (1) contacting at a temperature of from about 0° C. to about 25° C.,
    (a) a mixture of pyridine and methyl [methyliminocarbonyloxy]-ethanimidothioate, with
    (b) sulfur dichloride to form a reaction slurry, (2) cooling said slurry to a temperature of no greater than about 10° C., (3) quenching said slurry by the addition thereto of methanol at a temperature of no greater than about 10° C., (4) separating said bis-[O-(1-methylthioethylimino)-N-methylcarbamic acid]-N,N'-sulfide from said slurry and purifying by one or more washings with methanol, and (5) thereafter, recovering said bis-[O-(1-methylthioethylimino)-N-methylcarbamic acid]-N,N'-sulfide in a yield of at least about 80 weight percent, a purity of at least about 95 percent, and having an improved thermal stability.

17. The process of claim 16 wherein the ratio of methanol to methyl [methyliminocarbonyloxy]-ethanimidothioate is from about 3 to 1 to about 20 to 1.

18. The process of claim 17 wherein the said ratio is 6 to 1.

19. The process of claim 16 wherein said sulfur dichloride is added to said mixture at a rate wherein the reaction temperature does not rise above 25° C.

* * * * *